(12) United States Patent
Petry et al.

(10) Patent No.: US 11,717,281 B2
(45) Date of Patent: Aug. 8, 2023

(54) SURGICAL CONSTRUCTS WITH SHUTTLING LOOPS AND METHODS OF TISSUE FIXATION

(71) Applicant: Arthrex, Inc., Naples, FL (US)

(72) Inventors: Andrew C. Petry, Naples, FL (US); Thomas Dooney, Jr., Naples, FL (US); Bradford O. Parsons, Irvington, NY (US); John A. Sodeika, Naples, FL (US); Peter J. Dreyfuss, Naples, FL (US); Stephen S. Burkhart, Boerne, TX (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 17/824,192

(22) Filed: May 25, 2022

(65) Prior Publication Data

US 2022/0287704 A1    Sep. 15, 2022

Related U.S. Application Data

(63) Continuation of application No. 15/997,062, filed on Jun. 4, 2018, now Pat. No. 11,350,923.

(51) Int. Cl.
*A61B 17/04* (2006.01)
*A61F 2/08* (2006.01)
*A61B 17/06* (2006.01)

(52) U.S. Cl.
CPC ...... *A61B 17/0401* (2013.01); *A61B 17/0487* (2013.01); *A61B 17/06166* (2013.01); *A61F 2/0811* (2013.01); *A61B 17/0466* (2013.01); *A61B 2017/0412* (2013.01); *A61B 2017/0414* (2013.01); *A61B 2017/0461* (2013.01)

(58) Field of Classification Search
CPC .......... A61B 17/0401; A61B 17/06166; A61B 17/0487; A61B 17/0466; A61B 2017/0412; A61B 2017/0414; A61B 2017/0461; A61F 2/0811
See application file for complete search history.

(56) References Cited

U.S. PATENT DOCUMENTS

| | | |
|---|---|---|
| 4,440,171 A | 4/1984 | Nomoto et al. |
| 4,962,757 A | 10/1990 | Stefan |
| 5,628,756 A | 5/1997 | Barker, Jr. et al. |
| 5,755,728 A | 5/1998 | Maki |
| 5,968,077 A | 10/1999 | Wojciechowicz et al. |
| 7,329,272 B2 | 2/2008 | Burkhart et al. |
| 7,749,250 B2 | 7/2010 | Stone et al. |
| 7,857,830 B2 | 12/2010 | Stone et al. |
| 7,892,256 B2 | 2/2011 | Grafton et al. |
| 7,905,903 B2 | 3/2011 | Stone et al. |
| 7,959,650 B2 | 6/2011 | Kaiser et al. |
| 7,981,140 B2 | 7/2011 | Burkhart |

(Continued)

FOREIGN PATENT DOCUMENTS

EP    2774546 A1    9/2014

*Primary Examiner* — Kathleen S Holwerda
(74) *Attorney, Agent, or Firm* — Potomac Law Group, PLLC (57) ABSTRACT

Knotless surgical constructs and methods of tissue repairs. A surgical construct can offer both repair and shuttling capabilities to allow for a single pass to load multiple sutures at once. A surgical construct can pass or shuttle multiple repair sutures while making a single pass through or around soft tissue.

17 Claims, 10 Drawing Sheets

(56) References Cited

U.S. PATENT DOCUMENTS

| | | | |
|---|---|---|---|
| 8,088,130 B2 | 1/2012 | Kaiser et al. | |
| 8,118,836 B2 | 2/2012 | Denham et al. | |
| 8,231,654 B2 | 7/2012 | Kaiser et al. | |
| 8,273,106 B2 | 9/2012 | Stone et al. | |
| 8,298,262 B2 | 10/2012 | Stone et al. | |
| 8,361,113 B2 | 1/2013 | Stone et al. | |
| 8,512,373 B2 | 8/2013 | Gilson et al. | |
| 8,562,645 B2 | 10/2013 | Stone et al. | |
| 8,562,647 B2 | 10/2013 | Kaiser et al. | |
| 8,652,172 B2 | 2/2014 | Denham et al. | |
| 8,834,521 B2 * | 9/2014 | Pinto | A61F 2/0811 606/228 |
| 8,840,645 B2 | 9/2014 | Denham et al. | |
| 8,876,900 B2 | 11/2014 | Guederian et al. | |
| 8,936,621 B2 | 1/2015 | Denham et al. | |
| 9,066,716 B2 | 6/2015 | Sikora et al. | |
| 9,149,267 B2 | 10/2015 | Norton et al. | |
| 9,179,950 B2 | 11/2015 | Zajac et al. | |
| 9,301,745 B2 | 4/2016 | Dreyfuss | |
| 9,314,241 B2 | 4/2016 | Stone et al. | |
| 9,332,979 B2 | 5/2016 | Sullivan et al. | |
| 9,357,992 B2 | 6/2016 | Stone et al. | |
| 9,370,350 B2 | 6/2016 | Norton | |
| 9,402,620 B2 | 8/2016 | Pilgeram | |
| 9,421,008 B2 | 8/2016 | Burkhart et al. | |
| 9,492,158 B2 | 11/2016 | Stone et al. | |
| 9,492,200 B2 | 11/2016 | Sikora et al. | |
| 9,532,777 B2 | 1/2017 | Kaiser et al. | |
| 9,539,003 B2 | 1/2017 | Stone et al. | |
| 9,603,591 B2 | 3/2017 | Denham et al. | |
| 9,974,534 B2 | 5/2018 | Troxel et al. | |
| 10,070,856 B1 | 9/2018 | Black et al. | |
| 10,172,606 B2 | 1/2019 | Sullivan et al. | |
| 10,610,212 B2 | 4/2020 | Breslich | |
| 2003/0130694 A1 | 7/2003 | Bojarski et al. | |
| 2003/0153947 A1 | 8/2003 | Koseki | |
| 2004/0106847 A1 | 6/2004 | Benderev | |
| 2005/0192631 A1 | 9/2005 | Grafton | |
| 2008/0086171 A1 | 4/2008 | Knapp et al. | |
| 2009/0312776 A1 | 12/2009 | Kaiser et al. | |
| 2011/0264141 A1 * | 10/2011 | Denham | A61B 17/0401 606/232 |
| 2012/0130422 A1 | 5/2012 | Hootstein | |
| 2012/0232655 A1 | 9/2012 | Lorrison et al. | |
| 2012/0290003 A1 | 11/2012 | Dreyfuss | |
| 2013/0023928 A1 * | 1/2013 | Dreyfuss | A61B 17/06166 606/228 |
| 2013/0138123 A1 | 5/2013 | Stone et al. | |
| 2014/0052179 A1 | 2/2014 | Dreyfuss et al. | |
| 2014/0243891 A1 | 8/2014 | Schmieding et al. | |
| 2014/0249577 A1 | 9/2014 | Pilgeram | |
| 2014/0257384 A1 | 9/2014 | Dreyfuss et al. | |
| 2014/0275750 A1 | 9/2014 | Levine | |
| 2015/0025552 A1 | 1/2015 | Stoll | |
| 2015/0066079 A1 | 3/2015 | Schmieding | |
| 2015/0335327 A1 | 11/2015 | Ferguson et al. | |
| 2017/0311947 A1 | 11/2017 | Kaiser et al. | |

\* cited by examiner

SURGICAL CONSTRUCTS WITH SHUTTLING LOOPS AND METHODS OF TISSUE FIXATION

CROSS-REFERENCE TO RELATED APPLICATIONS

This application is a continuation of, and claims priority benefit from, U.S. application Ser. No. 15/997,062, filed Jun. 4, 2018, the disclosure of which is incorporated by reference in its entirety herein.

BACKGROUND

The disclosure relates to surgical devices and, more specifically, to knotless suture constructs and associated methods of tissue repairs.

SUMMARY

Knotless surgical constructs and methods of tissue repairs are disclosed. A surgical construct can offer both repair and shuttling capabilities to allow for a single pass to load multiple sutures at once. The surgical construct can pass or shuttle multiple repair sutures while making a single pass through or around soft tissue.

Methods of tissue repair are also disclosed. In an embodiment, a repair suture is passed with a suture passer while additional repair sutures are shuttled simultaneously without loading a separate shuttling stitch or wire.

DETAILED DESCRIPTION

The disclosure provides knotless surgical constructs for passing or shuttling at least one length of flexible material, for example suture such as high strength suture, tape, wire, cable, or fabric. The knotless surgical construct includes a suturing construct (for example, a flexible strand such as suture, or tape such as suture tape) provided with at least one shuttling loop that allows additional flexible strands to pass through tissue. In an embodiment, the suturing construct is provided with two or more shuffling loops. In an embodiment, at least one additional flexible strand is passed simultaneously with the suturing construct. In an embodiment, the suturing construct is a suture tape with two shuffling loops. In an embodiment, the suturing construct is a suture tape with two shuffling loops, the suture tape passing through an inner portion of a sleeve or tubular member. In an embodiment, one or more additional flexible strands are passed through one or more shuttling loops. In an embodiment, the surgical construct is pre-loaded on a fixation device such as a knotless fixation device to be secured within hard tissue such as bone. In an embodiment, the fixation device has a closed eyelet and the surgical construct is passed through the eyelet. In an embodiment, the fixation device has a closed eyelet and the surgical construct with at least another additional flexible strand are passed through the eyelet.

In an embodiment, a surgical construct comprises: a suturing construct with a middle region and two or more ends; two or more shuttling loops; and at least one end tail. The surgical construct may be knotless. The middle region may be a suture section with a gradual taper. The suture section may be suture tape. The two or more ends may be opposed ends. The suture tape may pass through open ends and along a longitudinal passage of a soft anchor sleeve or tubular member. The shuttling loops may be provided each at a corresponding end. The shuttling loops may provide passing of one or more lengths of flexible material, for example, strands such as suture, for example, high strength suture, tape, suture tape, combination of suture and tape, wire, cable, or fabric, among many others. One or more lengths of flexible material may pass through one or more shuttling loops.

In another embodiment, a knotless surgical construct comprises: a flexible construct with a middle region and two tail regions; two shuttling loops, each loop being provided between the middle region and an end of a tail region; and at least another flexible strand passed through at least one of the two shuttling loops. The flexible construct may be a repair suture. The loops may be provided below a distal portion of the repair suture. The loops may be located on each side of the repair suture, allowing for one pass or two separate passes with shuttling capabilities. The middle region may be a suture section with a gradual taper. The suture section may be suture tape. The suture tape may pass through open ends and through a longitudinal inner passage of a soft anchor sleeve or tubular member. The two tail regions may have a diameter smaller than that of the middle region. The flexible strand may be suture such as high strength suture, tape, suture tape, combination of suture and tape, wire, cable, or fabric, among many others. The middle region may be suture tape. The tail regions may be round suture.

In another embodiment, a knotless surgical construct comprises: a suturing construct with a middle region and two tail regions forming a closed loop and terminating in a single tail; two shuttling loops, each loop being located between the middle region and an end of the single tail; and at least another flexible strand passed through at least one of the two shuttling loops. The middle region may be a suture section with a gradual taper. The two tail regions may terminate in a single tail. The single tail may be a spliced tail. The single tail may be a swedged end. The single tail may be formed by splicing, bonding, gluing or bringing together at least two portions of the two tail regions. After the surgical construct is passed through tissue, the splice or single tail may be cut to open the closed loop and allow the construct to have again two tail regions, each tail region with a corresponding shuttling loop. The two tail regions may have a diameter smaller than that of the middle region. The flexible strand may be suture such as high strength suture, tape, suture tape, combination of suture and tape, wire, cable, or fabric, among many others. The middle region may be suture tape. The tail regions may be round suture. One or more flexible strands may pass through one or more shuttling loops. The suture tape and the one or more flexible strands may pass through open ends and through a longitudinal inner passage of a soft anchor sleeve or tubular member.

Methods of tissue repair are also disclosed. In an embodiment, additional flexible strands (additional repair strands) can be passed simultaneously with the repair suture by conducting a single pass through tissue to be repaired (ligament, tendon, graft, etc.). The repair suture and the additional flexible strands may be passed and/or shuttled simultaneously with a surgical instrument such as a suture passer. The repair suture and the additional flexible strands may be passed or shuttled simultaneously without loading a separate shuttling stitch or wire, and without passing each strand independently. The repair suture may include a middle region with two ends and two shuttling loops, a first shuffling loop being provided at one of the two ends, and a second shuttling loop being provided at the other of the two ends. The middle region may be in the form of a suture tape. The shuttling loops facilitate shuttling the additional flexible strands (additional repair sutures) simultaneously with the repair suture. One or more additional flexible strands may pass through one or more shuttling loops.

A method of tissue repair (for example, soft tissue to bone fixation) includes passing a surgical construct through tissue and securing the tissue with the surgical construct. The surgical construct may be passed through or around tissue by loading the surgical construct onto a suture passer and simultaneously shuffling a repair strand together with additional repair strands. The additional repair strands are passed through shuttling loops of the surgical construct and passed/shuttled through or around tissue without the need to pass each additional repair strand individually. A single pass loads multiple repair strands at once.

The surgical constructs and methods of the present disclosure provide apparatus and methods for tissue repair, for example, rotator cuff repair. The surgical constructs allow for a single or two separate passes with shuttling capabilities, and help simplify shuttling and managing of suture in a tissue repair such as rotator cuff repair. The surgical constructs and associated methods offer the repair construct and shuttling capabilities in one, to allow for a single pass to load multiple sutures at once.

Referring now to the drawings, where like elements are designated by like reference numerals, FIGS. 1-4 illustrate structural components of surgical construct 100, 200, 300 (construct 100, 200, 300; suture construct 100, 200, 300; knotless surgical construct 100, 200, 300) of the present disclosure. FIGS. 5-15 illustrate steps of a method of tissue repair with the surgical construct 100, 200, 300.

Figure 1:
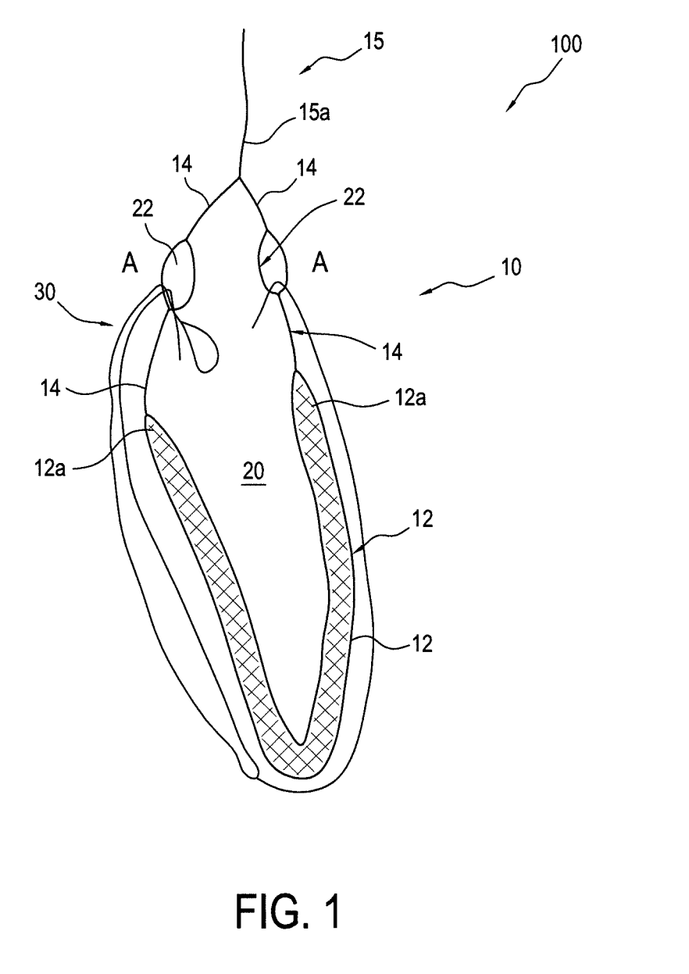
FIG. 1 illustrates a surgical construct according to an exemplary embodiment.
Figure 2:
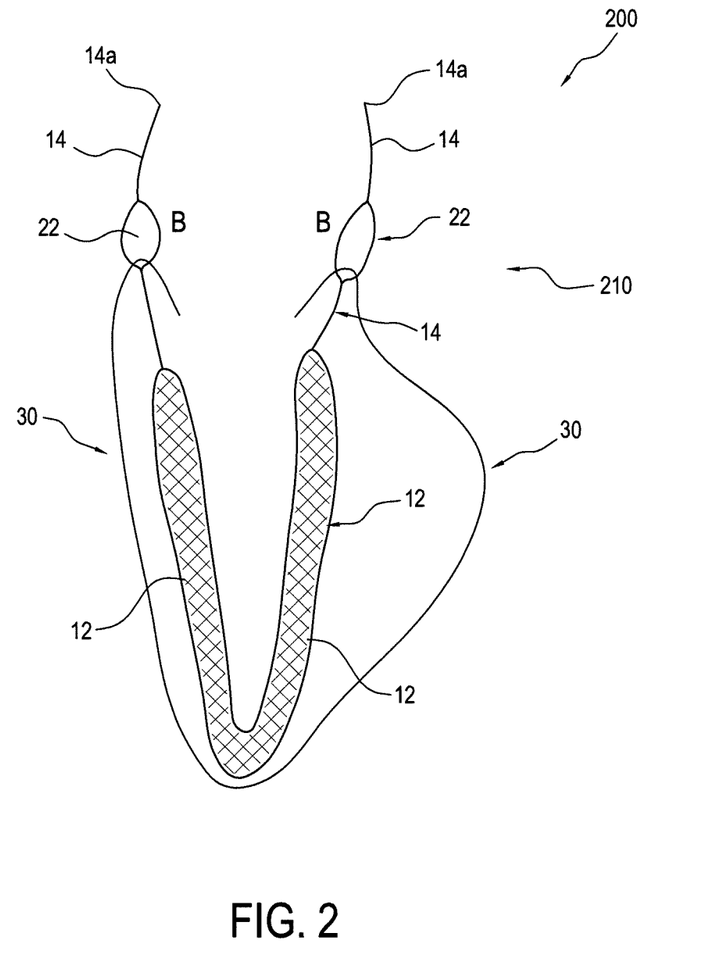
FIG. 2 illustrates a surgical construct according to another exemplary embodiment.
Figure 3:
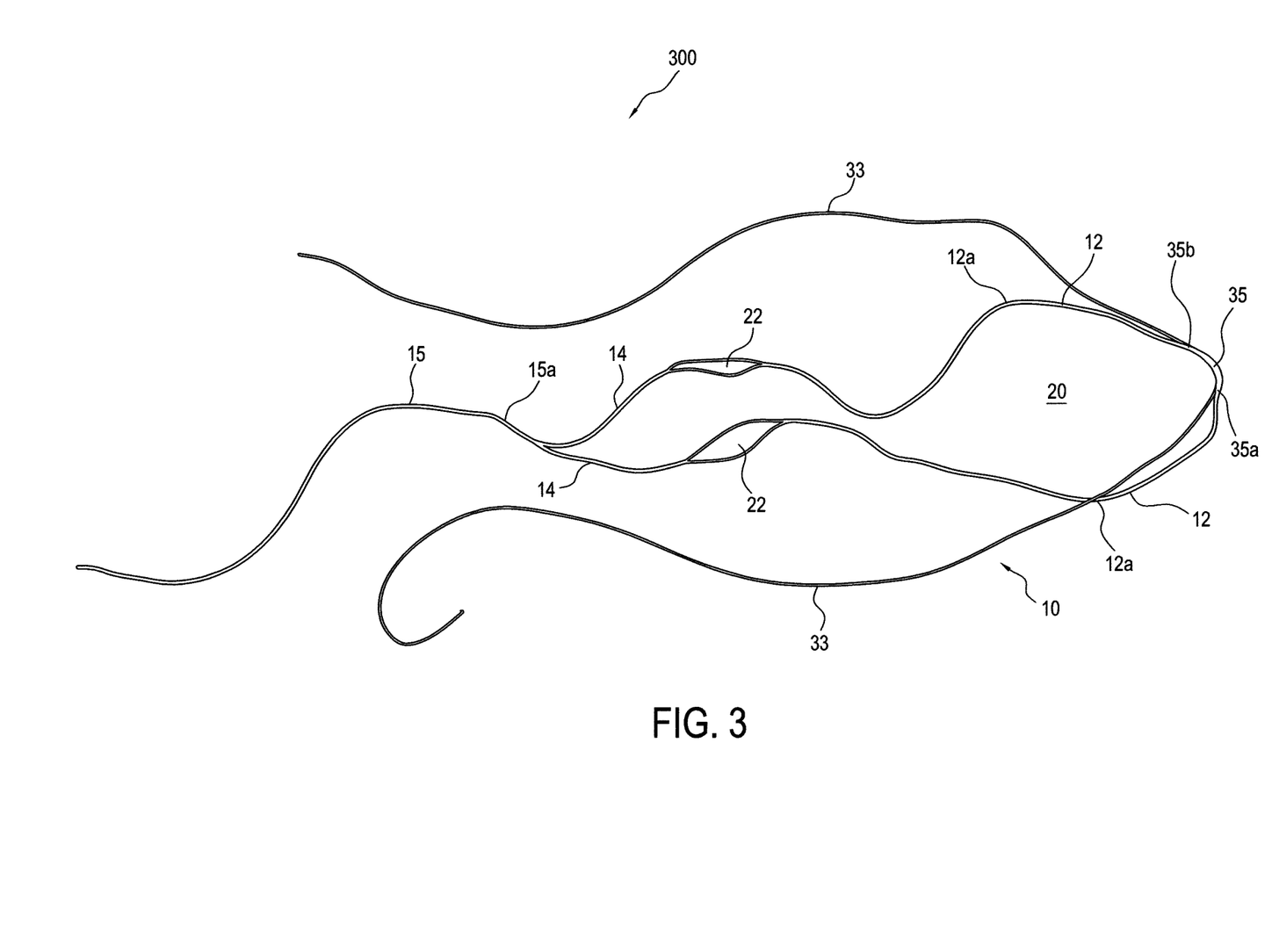
FIGS. 3 and 4 illustrate a surgical construct according to another exemplary embodiment.
Figure 4:
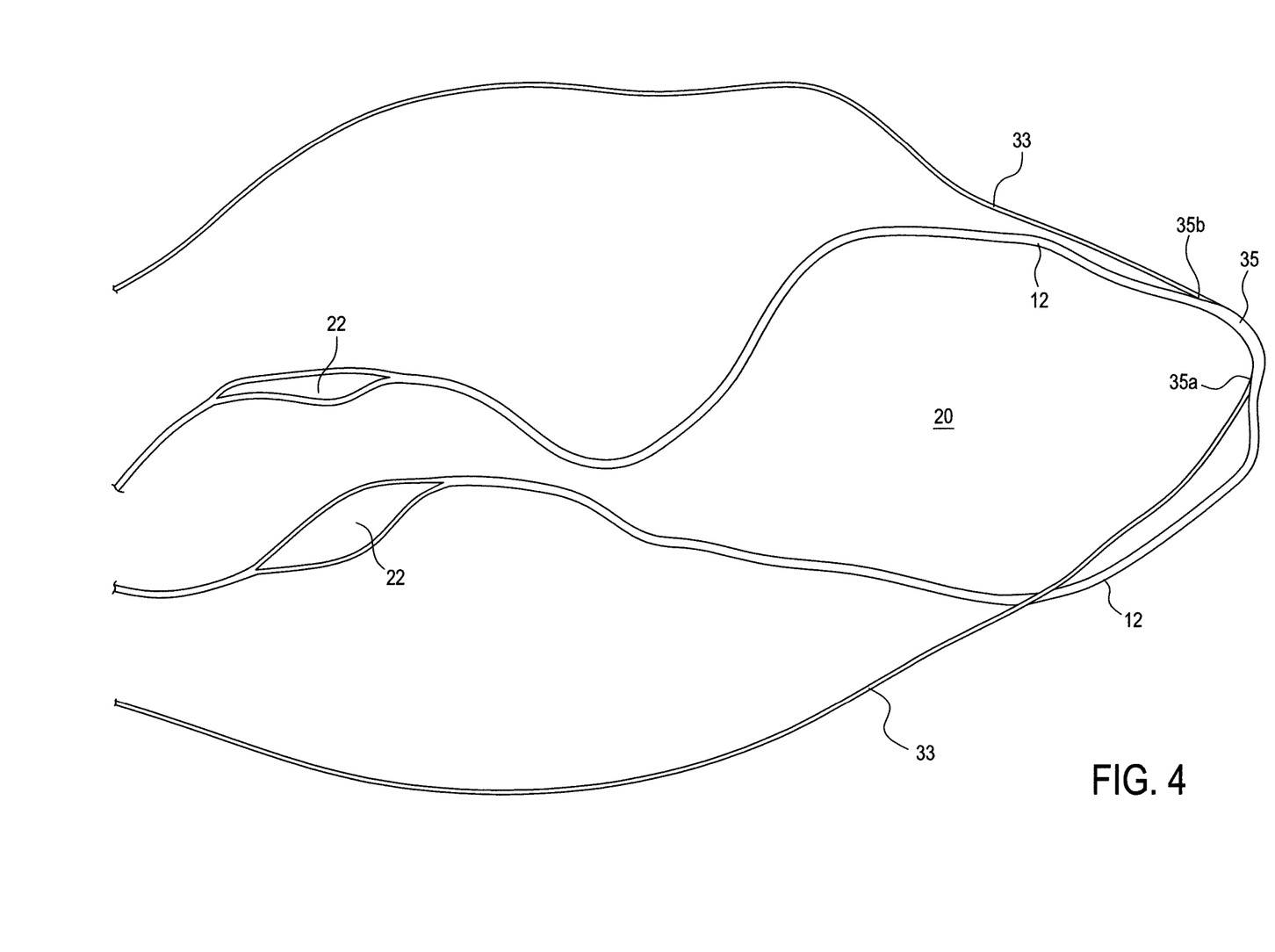

FIG. 1 illustrates exemplary surgical construct 100 which is a single-tail construct. FIG. 2 illustrates another exemplary surgical construct 200 which is a two-tail construct. FIGS. 3 and 4 illustrate exemplary surgical construct 300 which is another single-tail construct.

Surgical construct 100 includes a suturing construct 10 with a middle region 12 and two tail regions 14 forming a closed loop 20 and terminating in a single tail 15 (spliced single tail 15 with splice 15a; or combined region 15); two shuttling loops 22 (eyelets 22 or closed loops 22), each loop 22 being provided between the middle region 12 and the single tail 15; and at least another flexible strand 30 passed through at least one of the two shuttling loops 22. The middle region 12 may be a suture section with a gradual taper 12a. The middle region 12 may be a suture tape with a gradual taper 12a. The two tail regions 14 (tails 14 or ends 14) form single tail 15 (terminate in single tail 15). The single tail 15 may be a spliced tail.

The middle region 12 has a first diameter and the opposing tail regions 14 have a second diameter, which is smaller than the first diameter. The tail regions 14 may have similar or different diameters. As illustrated in FIG. 1, each of the diameters of the tail regions 14 is smaller than the diameter of the middle region 12. Tail regions 14 may have similar or different lengths and/or similar or different diameters. Because of the thin spliced single tail 15, the suture construct 100 can be easily inserted into suture/tape passing and retrieving instruments (such as the Arthrex Scorpion®) and passed through soft tissue (such as a rotator cuff). Once the suture construct 100 has been passed, the splice 15 may be cut to open closed loop 20 and allow the suture/tape to have again individual tail regions 14.

FIG. 1 also illustrated two shuttling loops 22. In the exemplary embodiment of FIG. 1, each loop 22 is provided at a point A located between the middle region 12 and a most proximal end of the spliced single tail 15. Shuffling loops 22 are flexible, continuous loops that may have similar or different diameters and/or similar or different perimeters. Shuttling loops may be formed of suture or any similar material. In an embodiment, shuttling loops 22 are formed of same material that forms tail regions 14, for example, round suture. Shuttling loops 22 may be formed of a high strength suture material with surgically-useful qualities such as Arthrex FiberWire® suture disclosed in U.S. Pat. No. 6,716,234, the entire disclosure of which is incorporated herein by reference. In an embodiment, at least one of shuffling loops 22 is flexible. In an embodiment, at least one of shuttling loops 22 is formed of a material (for example, alloy or metal) which does not itself has to be flexible but allows the suturing construct to "flex."

Shuttling loops 22 allow at least another flexible strand 30 to pass therethrough. Flexible strand 30 may be any additional repair strand, for example, suture strands, nitinol strands, FiberLink™ among many others. One or more flexible strands 30 may pass through one or more shuttling loops 22.

Middle region 12 may have cross-sections of various forms and geometries, including round, oval, rectangular, or flat, among others, or combination of such forms and geometries. In an exemplary embodiment only, middle region 12 may be provided as a suture tape or as a round suture, or as a combination of rape and round suture. The diameter of middle region 12 may be constant or may vary. Preferably, the diameter of region 12 is constant and is greater than the diameter of tail regions 14 and of the spliced single tail 15. The middle region 12 can be any suture strand or suture tape, for example. Arthrex FiberTape®, which is a high strength suture tape that is braided and rectangular-like in cross section and as disclosed in U.S. Pat. No. 7,892,256, the disclosure of which is incorporated by reference in its entirety herein. However, the surgical constructs 100, 200, 300 can be used with any type of flexible material or suture known in the art.

FIG. 2 illustrates surgical construct 200 which is similar to surgical construct 100 detailed above, except that surgical construct 200 does not include closed loop 20 and spliced single tail 15, i.e., two-tail construct at the time of manufacturing. Surgical construct 200 includes suturing construct 110 with a middle region 12 and two tail regions 14; two shuttling loops 22, each loop 22 being provided at a location between the middle region 12 and a most distal end of the tail region 14; and at least another flexible strand 30 passed through at least one of the two shuttling loops 22. In an embodiment, each loop 22 is provided at a point B located between the middle region 12 and a most distal end 14a of tail region 14.

FIGS. 3 and 4 illustrate surgical construct 300 which is similar to surgical construct 100 detailed above in that it is also a single-tail construct, except that surgical construct 300 includes at least an additional flexible strand or flexible material 33 which is passed together with suturing construct 10 through a soft anchor sleeve 35 (sheath 35; sleeve 35; tubular member 35). The body of the soft anchor sleeve 35 allows the middle region 12 and the at least an additional flexible material or flexible strand 35 to extend through at least an inner portion of the body. Soft anchor sleeve 35 is provided with a first open end 35a and a second open end 35b. The flexible strand or flexible material 33 may be a repair suture that passes through the soft anchor. The construct may be provided with a sliding shuttle stitch (for example, a #2 TigerTail® suture) loaded with the repair suture and further spliced to form a splice. The splice may be located wholly or mostly within the sheath.

Surgical construct 300 includes suturing construct 10 with a middle region 12 and two tail regions 14; two shuttling loops 22, each loop 22 being provided at a location between the middle region 12 and a most distal end of the tail region 14; and at least another flexible strand 33 which may be passed through at least one of the two shuttling loops 22. Like the surgical construct 100, once the suture construct 300 has been passed, the splice 15 may be cut to open closed loop 20 and allow the suture/tape to have again individual tail regions 14.

Figure 5:
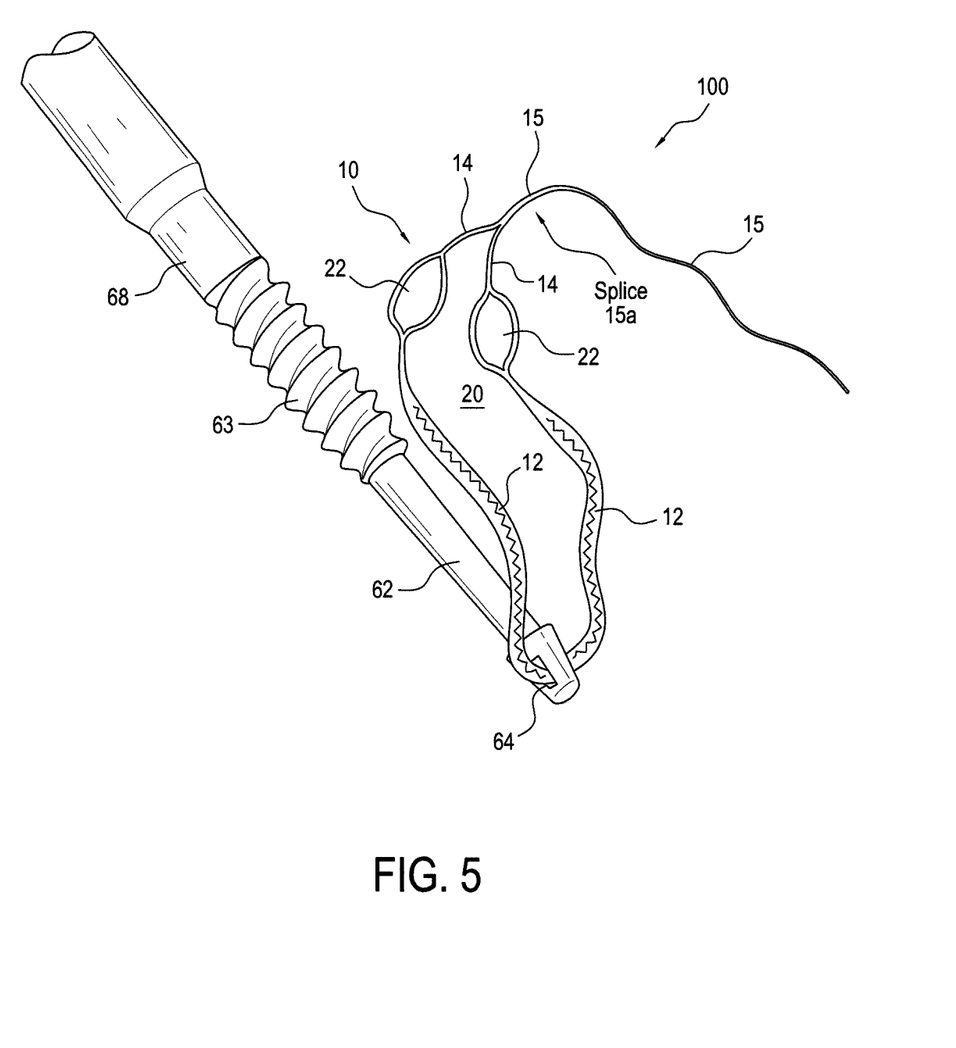
FIGS. 5-15 illustrate an exemplary method of tissue repair with a surgical construct.

FIG. 5 illustrates exemplary surgical construct 100 threaded through a knotless fixation device 62 such as an Arthrex Push Lock® C anchor (as disclosed and described in U.S. Pat. No. 7,329,272, the disclosure of which is incorporated by reference in its entirety herein) or an Arthrex SwiveLock® C anchor (as disclosed and described in U.S. Pat. No. 8,012,174, the disclosure of which is incorporated by reference in its entirety herein). The fixation device 62 comprises an anchor body (or screw) 63 and an eyelet 64.

As shown in FIG. 5, construct 100 is pre-loaded (manufactured) on the fixation device 62 (i.e., surgical construct 100 is pre-loaded through eyelet 64 of the knotless fixation device 62 (SwiveLock® anchor 62)). As described in more detail below, the fixation device 62 with the pre-loaded construct 100 is first inserted into a bone socket or tunnel. Subsequent to the insertion into the bone socket, the single tail 15 together with any additional flexible strands 30 passed through one or more shuttling loops 22 are passed through the tissue to be repaired. After passing the surgical construct 100 through the tissue (with the advantage of a single tail 15), the splice is cut to open closed loop 20 of the construct and to form again two ends of the suture or suture tape. Each of the two ends (each end provided with the corresponding shuttling loop 22 with any additional flexible strands 30) may be employed further for tissue fixation, for example, the two ends and/or any additional flexible strands 30 may be individually and/or together threaded through additional eyelets of additional fixation devices and may be inserted in additional pilot holes (with additional fixation devices) to complete the suture repair system. Construct 300 may be also pre-loaded onto fixation device 62 (similarly to construct 100) except that soft anchor sleeve 35 may be passed through eyelet 64 of the knotless fixation device 62 and secured into bone.

The surgical constructs 100, 200, 300 may be employed for various tissue repairs, for example, soft tissue to bone repairs. The tissue repairs may employ at least one knotless fixation device. The knotless fixation devices may be knotless anchors, for example, swivel and/or screw-in suture anchors and/or push-in anchors (such as an Arthrex SwiveLock® anchor or a RushLock® Anchor).

According to an exemplary embodiment only, the surgical construct 100, 200, 300 of the present disclosure may be employed in a method for double row fixation of tendon to bone, as detailed in U.S. Pat. No. 8,012,174. A method of exemplary tissue fixation with the surgical construct 100 comprises inter alia the steps of: (i) providing surgical construct 100 pre-loaded (manufactured) on a fixation device (for example, a knotless fixation device); (ii) securing the fixation device with the pre-loaded construct 100 into a bone socket or tunnel; (iii) passing the surgical construct 100 through tissue to be repaired; (iv) removing the splice of the surgical construct 100 to release the two tail regions of the construct, each tail with corresponding shuttling loop 22 with at least one additional flexible strand 30 passed therethrough; and (v) employing at least one of the two released tail regions and/or additional flexible strands to fixate tissue.

Figure 6:
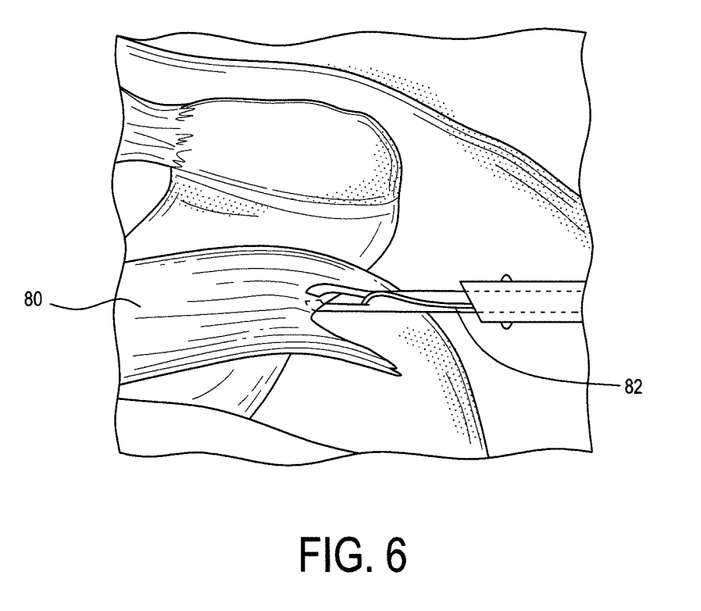

Reference is now made to FIGS. 6-15 which illustrate subsequent steps of a method of soft tissue repair (arthroscopic rotator cuff repair) with the surgical construct 100 of FIG. 1, and according to an exemplary embodiment. FIG. 6 illustrates a side view of a human shoulder of a patient undergoing a repair of rotator cuff 80 in accordance with an exemplary embodiment of the present disclosure. Although this particular embodiment will be illustrated below with reference to FIGS. 6-15 and with reference to only a particular knotless fixation device ((such Arthrex SwiveLock® C anchor), the disclosure is not limited to this particular embodiment and contemplates additional embodiments wherein any knotless fixation device may be employed, depending on the characteristics of the repair site and of the particular application.

The mobility of the tear is assessed using, for example, a tissue grasper 82 (FIG. 6) such as the Arthrex KingFisher™ Suture Retriever/Tissue Grasper, to determine whether a U or L-shaped component exists.

Figure 7:
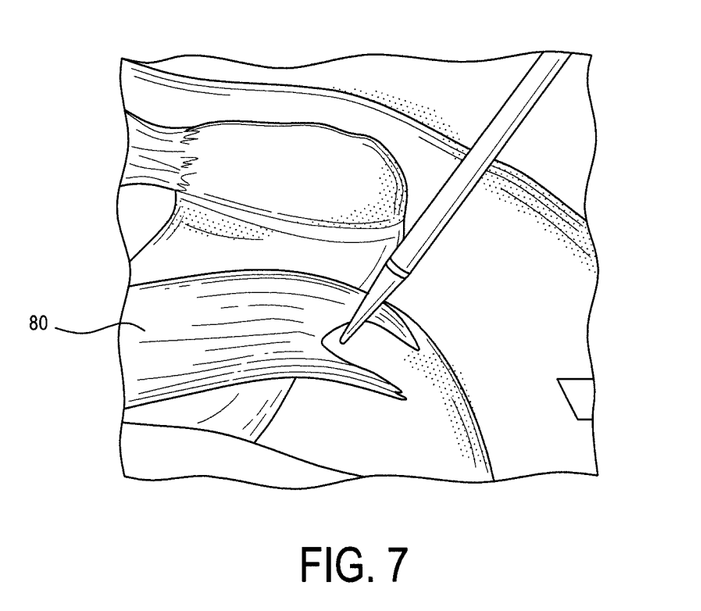

FIG. 7 illustrates the preparation of two pilot holes 60 for two suture anchors that will be inserted in the medial row. A punch may be employed adjacent to the articular margin of the humerus and at about 45 degree angle to form the two pilot holes. Subsequent to the formation of the pilot holes 60, and as shown in FIGS. 8-11, two fixation devices 62 with a pre-loaded surgical construct 100 are placed in the preformed holes 60 in the medial row. These fixation devices assure full contact of the detached tendon 80 along the medial footprint of the greater tuberosity.

Figure 8:
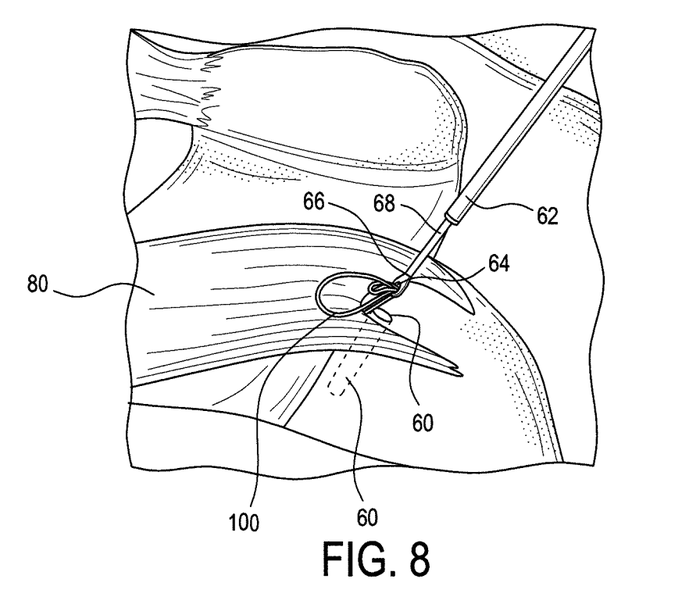

As illustrated in FIG. 8, surgical construct 100 is preloaded (manufactured) on the fixation device 62, i.e., the surgical construct 100 is pre-loaded through eyelet 64 of the knotless fixation device 62 (SwiveLock® anchor 62) on the distal end 66 of the driver 68.

Subsequently, and as shown in FIG. 8, the distal tip 66 of the knotless fixation device 62 (with the pre-loaded surgical construct 100) is brought to the edge of the pilot hole 60. The driver 68 is then completely advanced into the pilot hole 60 until the anchor body or screw 63 contacts the bone. The driver is rotated in a clockwise direction, for example, to complete insertion. A mallet may be employed to impact the anchor body 63 into the pilot hole 60 until the anchor body is flush with the humerus. The driver 68 is then turned counterclockwise to disengage the eyelet 64 (within pilot hole 60) from the driver shaft. The steps described above are subsequently repeated for the second knotless fixation device 62 (for example, a second SwiveLock® anchor) with another pre-loaded surgical construct 100.

Figure 9:
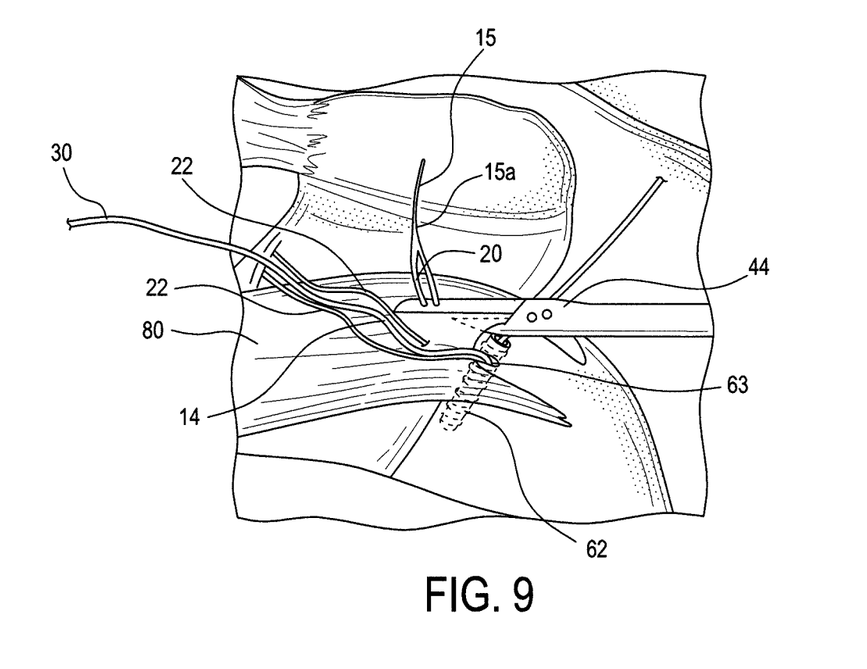

Subsequent to the securing of the knotless fixation devices 62 (with surgical construct 100 pre-loaded through eyelets 64 of the knotless fixation devices 62) within the hone sockets or tunnels, the tail 15 of the surgical construct 100 is passed through the tissue to be repaired, i.e., through rotator cuff 80. For example, and as shown in FIG. 9, a suture passing instrument 44 (such as an Arthrex Scorpion™) may be used to shuttle tail 15 through the rotator cuff 80. The tail 15 of the surgical construct 100 may be alternatively loaded through a shuttling device such as a Fiber-Link™ loop and then shuttled through the rotator cuff 80 (with a suture passing instrument). Because of the thin spliced tail region 15, the surgical construct 100 can be easily inserted into passing and retrieving instruments (such as the Arthrex Scorpion®) and passed easily through soft tissue (such as the rotator cuff 80).

For a two- or multiple-tail construct, such as surgical construct 200 of FIG. 2, the tail regions 14 may be passed through tissue by employing, for example, a suture shuttle (such as FiberLink™) and a suture passing instrument (such as an Arthrex Scorpion™ or similar instrument) to shuttle tail regions 14 with shuttling loops 22 and any additional flexible strands 30 through the rotator cuff 80. Because of the thin tail regions 14, the surgical construct 200 can be easily inserted into passing and retrieving instruments (such as the Arthrex FiberLink™. and/or Scorpion™) and passed easily through soft tissue (such as the rotator cuff 80). With any of surgical constructs 100, 200, 300, shuttling loops 22 may carry at least one flexible strand 30, 33 threaded through the loops, which is shuttled through the soft tissue together with the repair suture/tape in a single pass step.

Figure 10:
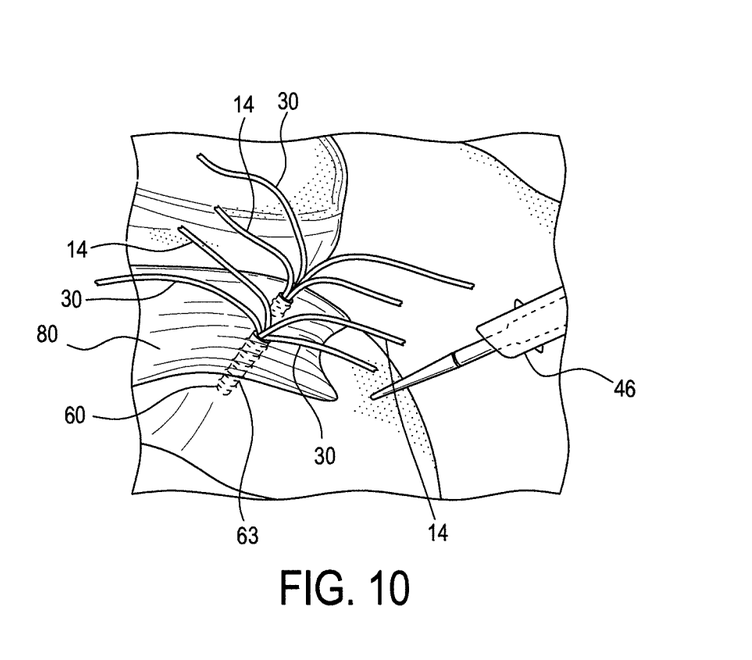
Figure 11:
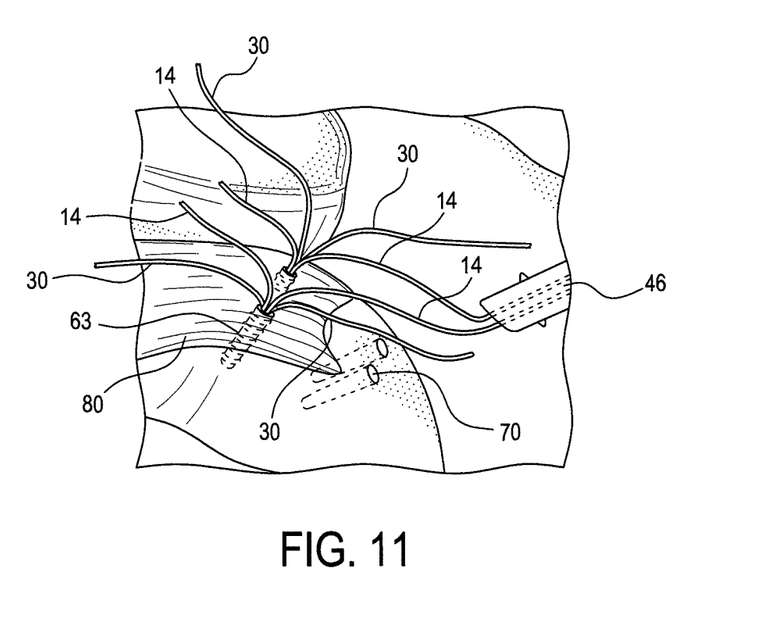
Figure 12:
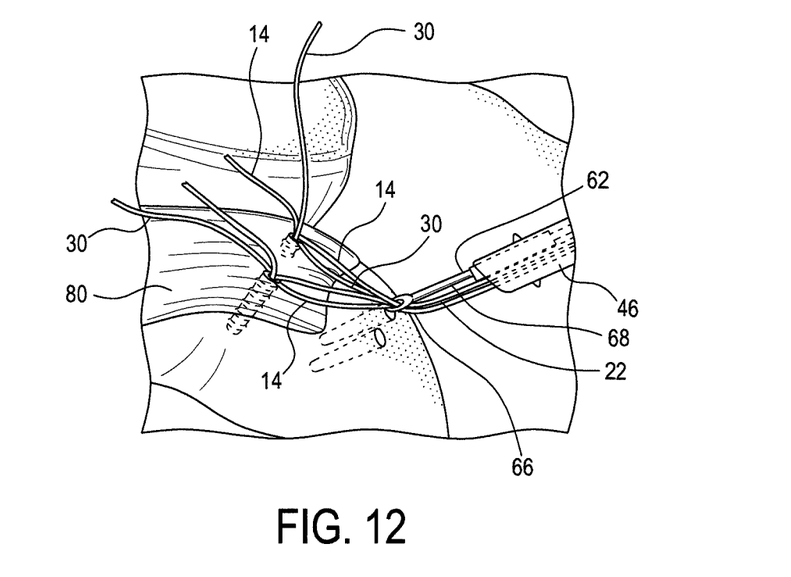
Figure 13:
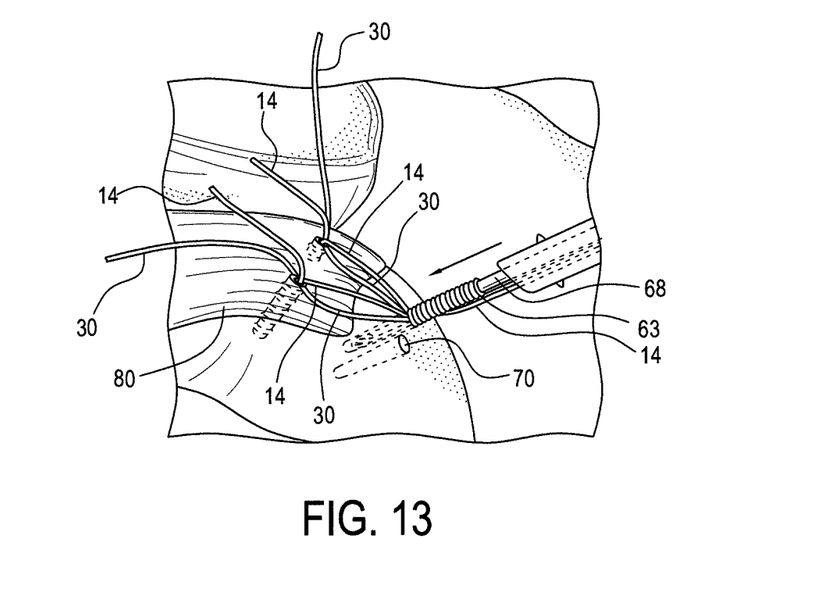
Figure 14:
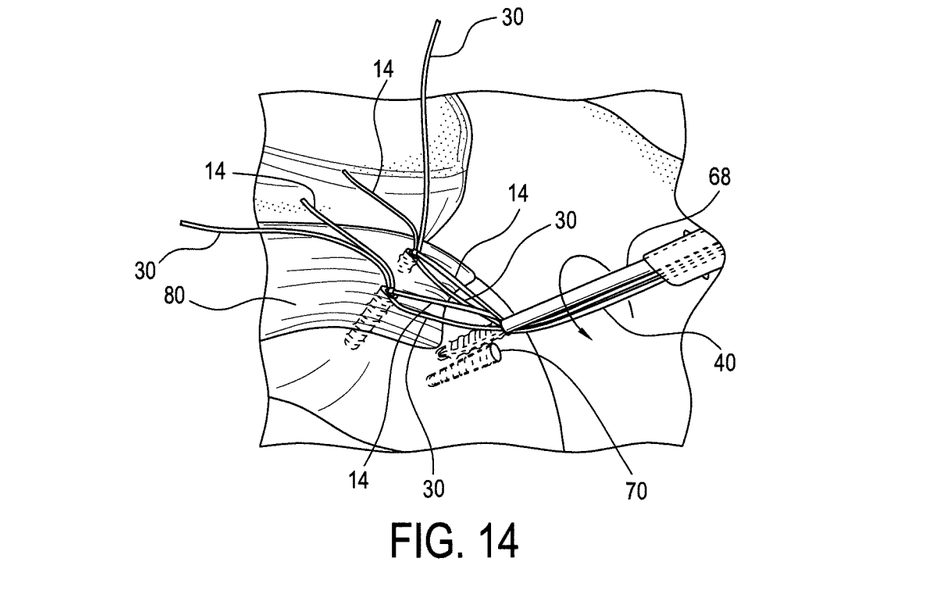

Reference is now made to FIGS. 9 and 10. Once the surgical construct 100 has been passed through tissue 80, the splice 15 is cut to allow the suture/tape to have again individual tails 14. FIG. 10 illustrates the two knotless fixation devices 62 with the two surgical constructs 100 having splices 15a removed (i.e., splice 15a is cut to open the loop 20 of the surgical construct and to form again two tails 14 of each of the constructs).

If desired, the shuttling loops 22 may be removed once additional flexible strands 30 have been shuttled through soft tissue. Alternatively, the shuttling loops 22 may be retained to aid in the tissue fixation repair. For simplicity, FIGS. 10-15 will illustrate only tail regions 14 (without shuttling loops 22) and with only one additional flexible strand 30 passed through the soft tissue. However, the disclosure is not limited to this exemplary-only embodiment and contemplates constructs with any number of shuffling loops that shuttle any number of additional flexible strands through tissue (together with the main repair strand). In addition, the steps set forth above with reference to surgical construct 100 have applicability to surgical construct 300, which is another single-tail construct.

Figure 15:
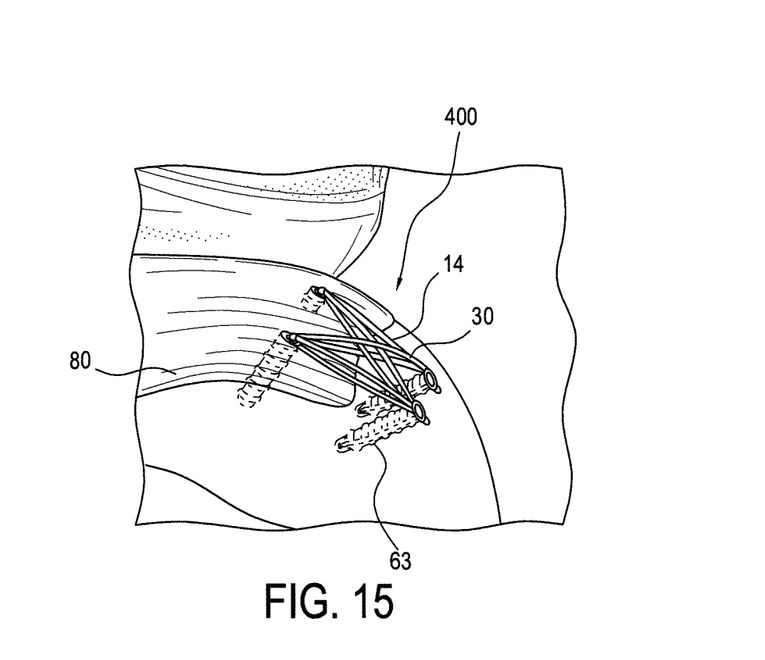

Each of the two ends 14 of the suture or suture tape—together with any additional flexible strands 30—may be employed further for tissue fixation. Each of the two ends 14 of the suture or suture tape and/or any additional flexible strands 30 may be additionally fixed within bone or similar tissue. In an exemplary embodiment only, each of the two ends and/or any of the additional flexible strands may be threaded through additional eyelets of additional fixation devices and may be inserted in additional pilot holes (with additional fixation devices) to complete various suture repairs of the present disclosure. In an exemplary embodiment only, one tail 14 from each of the anchors 62 is retrieved and then loaded through another fixation device (for example, through another fixation device 62) and inserted within pilot holes 70 (FIGS. 12-14) of a lateral row of the suture repair 400 (FIG. 15). Additional flexible strands 30 may be also inserted into the same or different pilot holes (together with tails 14 or without any of the tails 14) of the lateral row.

Tails 14 and/or additional flexible strands 30 are inserted into prepared lateral bone sockets 70 until the anchor body contacts the bone. Tension is adjusted if necessary. The SwiveLock® driver is rotated in a clockwise direction to complete insertion. The tails 14 and/or additional flexible strands 30 are cut, preferably one at a time, with an exemplary open-ended instrument (FiberWire® cutter) to complete formation of criss-cross suturing pattern 400 (FIG. 15) of the present disclosure.

The surgical constructs 100, 200, 300 described above may be formed of strands of a high strength suture material with surgically-useful qualities, including knot tie down characteristics and handling, such as Arthrex FiberWire® suture disclosed in U.S. Pat. No. 6,716,234, the entire disclosure of which is incorporated herein by reference. The surgical suture constructs may be formed of optional colored strands (preferably black) to assist surgeons in distinguishing between suture lengths with the trace and suture lengths without the trace. Preferably, each of tail regions 14 may be provided in different colors to assist surgeons in retrieving one tail from each of the knotless fixation devices and then loading them through another fixation device, during the formation of the criss-cross suturing pattern 400 (FIG. 15).

Surgical constructs 100, 200, 300 may be preferably coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

In additional embodiments, middle region 12 may be formed of polyester (for example, braided polyester) and the suture tail 15 with shuttling loops 22 may be also formed of polyester or a similar material. In an exemplary embodiment only, middle region 12 may be formed of braided polyester with a polyester core, and single tail 15 may be braided polyester with a polyester core and spliced to the suture. The middle region and tail may be coated as detailed above. In addition, a coating may be provided to the yarns forming the surgical constructs 100, 200, 300 before braiding. Polyester yarns for the braided construct of the middle region 12 may be coated using a silicone elastomer (or a similar material as detailed above) prior to braiding. Similarly, the suture tail regions 14 and/or shuttling loops 22 may be coated using the same or different coating material after braiding and before splicing. If desired, at least one of the tail regions 14 and/or single spliced tail 15 and/or at least one of shuttling loops 22 and/or at least one of the additional flexible strands 30, 33 of construct 100, 300 (preferably both tail regions 14, shuttling loops 22, and spliced tail 15, as well as the additional flexible strands 30, 33) may be coated, impregnated, or otherwise stiffened with a material such as plastic, for example. Preferably, end tail 15 may have a very fine end that is coated, impregnated, or stiffened with a material such as plastic, for example.

The tail regions 14, the shuttling loops 22, the single tail 15, and the additional flexible strands 30, 33 of the surgical constructs 100, 200, 300 may be also provided with tinted tracing strands, or otherwise contrast visually with the middle region of the suture construct, which remains a plain, solid color, or displays a different tracing pattern, for example. Accordingly, when the surgical construct is loaded through the eyelet of a suture anchor or passed through tissue, for example, at least one of the tail regions 14 of the suture construct, or at least one of the shuttling loops 22, or the single tail 15, or the middle region 12, or the additional flexible strand 30, may be visually coded, making identification and handling of the suture legs simpler. Easy identification of suture in situ is advantageous in surgical procedures, particularly during arthroscopic surgeries, such as endoscopy and laparoscopy.

The surgical construct 100, 200, 300 of the present disclosure has applicability to suture applications that may be employed in surgical procedures such as rotator cuff repair, Achilles tendon repair, patellar tendon repair, ACL/PCL reconstruction, hip and shoulder reconstruction procedures, and applications for suture used in or with suture anchors. In exemplary embodiments only, and as detailed above, the surgical suture construct of the present disclosure may be employed in suture applications that do not involve knot tying, for example, for use with suture anchors (such as PushLock® suture anchor) or for knotless arthroscopic suture repairs (such as knotless single row rotator cuff repair, or SpeedBridge™ repair using no knots and only suture passing steps), among many others.

Surgical constructs 100, 200, 300 may be used in an exemplary SutureBridge™ tendon repair technique, developed by Arthrex, Inc., and disclosed in U.S. Pat. No. 8,012,174 (the disclosure of which is herein incorporated by reference in its entirety) which consists of a tied medial row constructed with two threaded suture anchors, combined with knotless lateral fixation using two Arthrex PushLocks®. The construct, enhances footprint compression and promotes tendon healing-to-bone with minimal knot tying.

Surgical constructs 100, 200, 300 may be used in an exemplary SpeedBridge™ technique, also developed by Arthrex, Inc., and disclosed in U.S. Pat. No. 9,005,246 (the entire disclosure of which is herein incorporated by reference) which uses a threaded swivel anchor combined with FiberTape® to create a quick and secure SutureBridge™ construct with no knots and only two suture passing steps. In the SpeedBridge™ technique, a swivel anchor, preferably an Arthrex 4.75 mm SwiveLock® C, loaded with one strand of FiberTape®, is inserted into a medial bone socket. A suture shuttle such as FiberLink™ may be used to shuttle both FiberTape®. tails through the rotator cuff simultaneously. A FiberLink™ tail is passed through the rotator cuff using a suture passing instrument such as the Scorpion™. The tails of the FiberTape® are loaded through the FiberLink™ loop and shuttled through the rotator cuff. These steps are repeated for the second medial row anchor.

The novel FiberTape® with shuttling loops surgical construct 100, 200, 300 of the present disclosure is a suture tape with a repair suture 12 and a loop 22 below the distal portion of the suture 12 to allow the shuttling of additional repair sutures 30, 33 while making a single pass through tissue (e.g., the rotator cuff). The loops 22 may be on each side of the repair suture 12 allowing for one pass or two separate passes with shuttling capabilities. Exemplary construct 100, 300 detailed above consists of a length of FiberTape® 12 provided with two shuttling loops 22 and with a splice 15a leading to a single tail 15 that can be easily loaded into a tissue passing instrument. The surgeon could easily cut the splice/tail to again have two FiberTape® tails 14 each with a shuttling loop 22 for completing the repair (for example, a SpeedBridge™ or SutureBridge™ repair).

The suture tape construct 100, 200, 300 of the present disclosure offers both repair and shuttling capabilities to allow for a single pass to load multiple sutures at once. The FiberTape® with shuttling loops construct 100, 200, 300 offers the ability to pass a repair suture and to shuttle additional repair sutures simultaneously without loading a separate shuttling stitch or wire.

When a surgeon wants to incorporate multiple sutures in a repair, the surgeon must first pass a shuttling stitch or pass each strand independently. The FiberTape® with shuttling loops construct 100, 200, 300 simplifies shuttling and management of suture in tissue repair, for example, rotator cuff repair. The FiberTape® with shuttling loops construct 100, 200, 300 allows a surgeon to pass the tail with a suture passer such as the Arthrex Scorpion® or similar suture passer with a single pass that facilitates shuttling additional sutures simultaneously.

An exemplary method of tissue repair may comprise inter alia the steps of (i) threading at least one additional repair strand 30, 33 through at least one shuttling loop 22 of a surgical construct 100, 200, 300; and (ii) passing the at least one additional repair strand 30, 33 and the surgical construct 100, 200, 300 through or around tissue to be repaired. The at least one additional repair strand 30, 33 may be passed simultaneously with the repair suture 12 of the surgical construct 100, 200, 300.

Another exemplary method of tissue repair may comprise inter alia the steps of (i) loading surgical construct 100, 200, 300 onto a suture passer instrument; (ii) passing repair suture 12 and at least one additional repair suture 30, 33 simultaneously and through a first tissue to be repaired (for example, soft tissue); and (iii) securing the repair suture 12 and the at least one additional repair suture 30, 33 to a second tissue (for example, bone).

For the purposes of the present invention, the term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body. In a preferred embodiment of the invention, the suture comprises a high strength suture sold by Arthrex, Inc. under the tradename FiberWire®. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

What is claimed is:

1. A suture construct comprising:
   a first suture with a passage extending therethrough; and
   a second suture separable from the first suture, the second suture comprising:
   a middle region configured to pass through the passage of the first suture to connect the first and second sutures together;
   two tail regions respectively located at opposite first and second ends of the middle region, wherein ends of the two tail regions opposite the middle region terminate in a single tail to form a closed loop with the middle region; and
   a shuttling loop that connects the first end of the middle region to a first one of the tail regions without the middle region or the first one of the tail regions extending through the shuttling loop, wherein the first end of the middle region is directly connected to one end of the shuttling loop and the first one of the tail regions is directly connected to an opposite end of the shuttling loop.

2. The suture construct of claim 1, wherein the first suture forms a soft anchor.

3. The suture construct of claim 2, wherein the soft anchor is tubular and defines an inner cavity that forms the passage.

4. The suture construct of claim 1, wherein at least part of the middle region comprises suture tape, while the two tail regions and the shuttling loop are not formed with suture tape.

5. The suture construct of claim 1, further comprising a second shuttling loop that connects the second end of the middle region to a second one of the tail regions without the middle region or the second one of the tail regions extending through the second shuttling loop, wherein the second end of the middle region is directly connected to one end of the second shuttling loop and the second one of the tail regions is directly connected to an opposite end of the second shuttling loop.

6. The suture construct of claim 1, wherein no additional loops are formed on the second suture between the first suture and the shuttling loop and between the shuttling loop and an end of the first one of the tail regions opposite the middle region.

7. The suture construct of claim 1, further comprising a third suture that is separable from the first and second sutures, wherein the third suture is threadable through the shuttling loop to move the third suture together with the shuttling loop.

8. The suture construct of claim 7, wherein the third suture is configured to pass through the passage of the first suture to connect the first and third sutures together.

9. A suture construct comprising:
a middle region;
two tail regions respectively located at opposite first and second ends of the middle region; and
a single tail formed by ends of the two tail regions opposite the middle region, such that the two tail regions and the middle region form a closed loop;
wherein a shuttling loop connects the first end of the middle region to a first one of the tail regions without the middle region or the first one of the tail regions extending through the shuttling loop, and wherein the first end of the middle region is directly connected to one end of the shuttling loop and the first one of the tail regions is directly connected to an opposite end of the shuttling loop.

10. The suture construct of claim 9, wherein at least part of the middle region comprises suture tape, while the two tail regions and the shuttling loop are not formed with suture tape.

11. The suture construct of claim 9, further comprising a separate second suture with a passage extending therethrough, wherein the middle region is configured to pass through the passage of the second suture to connect to the second suture.

12. The suture construct of claim 11, wherein the second suture forms a soft anchor.

13. The suture construct of claim 11, further comprising a separate third suture that is configured to pass through the passage of the second suture to connect the second and third sutures together.

14. A fixation device comprising the suture construct of claim 9 and an anchor body.

15. The fixation device of claim 14, wherein the fixation device is a knotless fixation device.

16. A suture construct comprising:
a first suture with a passage extending therethrough;
a second suture separable from the first suture, the second suture comprising:
a middle region configured to pass through the passage of the first suture to connect the first and second sutures together;
two tail regions respectively located at opposite first and second ends of the middle region, wherein ends of the two tail regions opposite the middle region terminate in a single tail to form a closed loop with the middle region; and
a shuttling loop that directly connects the first end of the middle region to a first one of the tail regions; and
a third suture separable from the first and second sutures, wherein the third suture is configured to pass through the passage of the first suture to connect the first and third sutures together, and is threadable through the shuttling loop to move the third suture together with the shuttling loop.

17. The suture construct of claim 16, wherein the first suture forms a soft anchor.

\* \* \* \* \*